United States Patent [19]

Ramwell et al.

[11] Patent Number: 5,147,856

[45] Date of Patent: Sep. 15, 1992

[54] METHOD FOR INHIBITING BLOOD VESSEL BLOCKAGE USING OCTAPEPTIDE COMPOSITIONS

[75] Inventors: Peter W. Ramwell, McLean, Va.; Pierre Braquet, Garches, France

[73] Assignee: Societe de Conseils de Recherches et d'Applications Scientifiques (S.C.R.A.S.), Paris, France

[21] Appl. No.: 329,854

[22] Filed: Mar. 28, 1989

[30] Foreign Application Priority Data

Jun. 3, 1988 [GB] United Kingdom ............... 8813160

[51] Int. Cl.$^5$ ............................................. C07K 7/26
[52] U.S. Cl. ........................................ 514/16; 514/11; 514/12; 530/311
[58] Field of Search ................. 514/11, 12, 16, 806; 530/311

[56] References Cited

U.S. PATENT DOCUMENTS 4,485,101 11/1984 Coy et al. ............................... 514/12
4,663,309 5/1987 Kaiser et al. .......................... 514/11
4,853,371 8/1989 Coy et al. ............................... 514/12

*Primary Examiner*—Lester L. Lee
*Attorney, Agent, or Firm*—Birch, Stewart, Kolasch & Birch

[57] ABSTRACT

A method for inhibiting blood vessel blockage in a mammal particularly after a procedure such as angioplasty, an arterial bypass operation or an allograft transplant operation which comprises: administering to a mammal before, during and/or after the procedure an effective blood vessel blockage inhibiting amount of an octapeptide having the formula

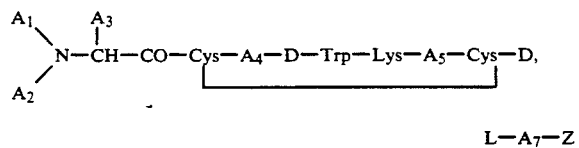

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2A_6$ (where $A_6$ is pentafluorophenyl, naphthyl, pyridyl, or phenyl); $A_4$ is o-, m- or, more preferably, p-substituted X-Phe (where X is a halogen, H, $NH_2$, $NO_2$, OH, or $C_{1-13}$ alkyl), pentafluoro-Phe, or β-Nal; $A_5$ is Thr, Ser, Phe, Val, α-aminobutyric acid, or Ile; $A_7$ is Thr, Trp, or β-Nal (and can be either the D- or L-isomer); and Z is $NH_2$ or OH; or a pharmaceutically acceptable salt thereof.

15 Claims, 4 Drawing Sheets

METHOD FOR INHIBITING BLOOD VESSEL BLOCKAGE USING OCTAPEPTIDE COMPOSITIONS

CROSS TO RELATED APPLICATIONS

This application is related to copending U.S. application Ser. No. 07/209,883 filed on Jun. 22, 1988, now U.S. Pat. No. 4,853,371, the entire contents of which are hereby incorporated by reference.

BACKGROUND OF THE INVENTION

This invention relates to the use of analogs of peptide hormones in human therapy.

A number of somatostatin analogs exhibiting OH-release-inhibiting activity have been described in the literature, including analogs containing fewer than the naturally occurring fourteen amino acids. For example, Coy et al, U.S. Pat. No. 4,485,101, hereby incorporated by reference, describes dodecapeptides having an N-terminal acetyl group, a C-terminal $NH_2$, D-Trp at position 6, and p-Cl-Phe at position 4. (Herein, when no designation of configuration is given, the L-isomer is intended).

The walls of blood vessels often are known to thicken and possibly block within a year after the vessels have been subjected to angioplasty. Similar thickening and blockage also is known to occur in artery grafts and in the vessels of transplanted tissue.

SUMMARY OF THE INVENTION

In general, the present invention is directed to a method of inhibiting blood vessel blockage in a mammal, e.g., a human, by administering to a patient a therapeutically effective amount of an octapeptide having the formula

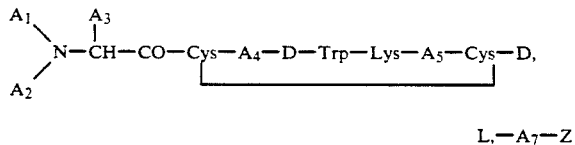

wherein each $A_1$ and $A_2$, independently, is H, $C_{1-12}$ alkyl, $C_{7-10}$ phenylalkyl, $R_1CO$ (where $R_1$ is $C_{1-20}$ alkyl, $C_{3-20}$ alkenyl, $C_{3-20}$ alkinyl, phenyl, naphthyl, or $C_{7-10}$ phenylalkyl), or $R_2OCO$ (where $R_2$ is $C_{1-10}$ alkyl or $C_{7-10}$ phenylalkyl), provided that when one of $A_1$ or $A_2$ is $R_1CO$ or $R_2OCO$, the other must be H; $A_3$ is $CH_2A_6$ (where $A_6$ is pentafluorophenyl, naphthyl, pyridyl, or phenyl); $A_4$ is o-, m- or, more preferably, p-substituted X-Phe (where X is a halogen, H, $NH_2$, $NO_2$, OH, or $C_{1-13}$ alkyl), pentafluoro-Phe, $\beta$-Nal; or $T_{4R}$ $A_5$ is Thr, Ser, Phe, Val, o-aminobutyric acid, or Ile; $A_7$ is Thr, Trp or $\beta$-Nal (and can be either the D- or L-isomer); and Z is $NH_2$ or OH; or a pharmaceutically acceptable salt thereof. The octapeptides provide effective inhibition against blood vessel blockage that can occur, e.g., following angioplasty, an arterial by-pass, or an organ transplant. Inhibiting blood vessel blockage, as used herein, is meant to include inhibition of the thickening of the vessel wall that can lead to blockage.

In the formula given above, the configuration of the molecule at the carbon atom to which $A_3$ is bonded can have the D- or L-configuration.

The invention features, in another aspect, a method of inhibiting transplant tissue (i.e., allograft) rejection in a mammal by administering an octapeptide of the above formula to a mammal into which the allograft has been transplanted. The octapeptide preferably is delivered in conjunction with cyclosporin.

In preferred embodiments, the Z in the administered octapeptide is $NH_2$, and

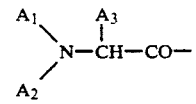

is D-$\beta$-napthylalanine. An example of preferred octapeptide is

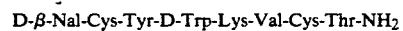

(angiopeptin), or a pharmaceutically acceptable salt thereof. Other examples of compounds within the above formula include

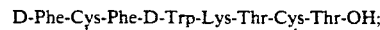

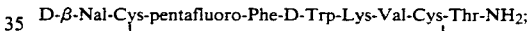

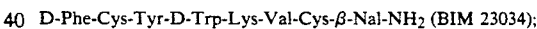

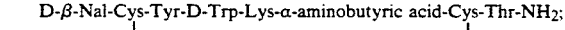

and

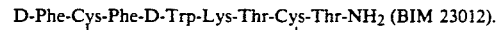

According to the invention, the composition administered preferably includes a therapeutically effective amount of the octapeptide and a pharmaceutically acceptable carrier substance (e.g., magnesium carbonate, lactose, or a phospholipid with which the therapeutic compound can form a micelle). The most preferred carrier substance is mannitol. Examples of such compositions include a pill, tablet, capsule, or liquid for oral administration; and a liquid capable of being administered nasally as drops or spray, or a liquid capable of intravenous, parenteral, subcutaneous, or intraperitoneal administration. The pill, tablet or capsule can be coated with a substance capable of protecting the composition from the gastric acid in the patient's stomach for a period of time sufficient to allow the composition to pass undisintegrated into the patient's small intestine. The therapeutic composition can also be administered in the form of an oil emulsion or dispersion in conjunction with a lipophilic salt such as pamoic acid. The therapeutic composition can also be in the form of a biodegradable sustained release formulation. For example, 10 mg of the compound can be formulated into a sustained release form and administered by injection every 2 to 3 weeks. For maximum efficacy, zero order release is desired. Zero order release can be obtained using an implantable or external pump to administer the therapeutic composition.

Use

The octapeptides can be used to inhibit blood vessel blockage in situations where there is an increased risk of such blockage occurring, such as following angioplasty (dilation of a blood vessel by physical means, e.g., a balloon catheter, a laser, or a rotating blade); an arterial by-pass operation (or other manipulation of a blood vessel, e.g., suturing a tear in a damaged vessel); or an allograft transplant operation in which blood vessels of the transplanted allograft are attached to blood vessels of the transplant recipient.

The octapeptides preferably are administered to the mammal continually (either continuously or at intervals) for at least 24 hours (more preferably, at least 48 hours) prior to and up to six months subsequent to performing the procedure giving rise to high risk situation to maintain the compound in the bloodstream continuously for this period of time. Generally, the octapeptides are most effective when also administered during the procedure. The compounds, when administered subcutaneously, should be administered to the mammal in a dosage of 1-100 µg/kg/day, preferably 20-100 µg/kg/day. The octapeptides are non-toxic at these dosages. Somewhat lower dosages can be used when the administration is intravenous; for oral administration, higher dosages can be used.

The octapeptides, when administered in a manner analogous to that described above, are also effective in inhibiting the rejection of transplanted tissue. Preferably, the compounds are administered in conjunction with standard dosages of cyclosporin. The octapeptides can inhibit corneal transplant rejection; for corneal transplants, topical administration, e.g., as a standard cream, gel, spray, or ointment, preferably is used.

Other features and advantages of the invention will be apparent from the following description of the preferred embodiments thereof.

BRIEF DESCRIPTION OF THE DRAWINGS

In FIG. 1

Figure 2:
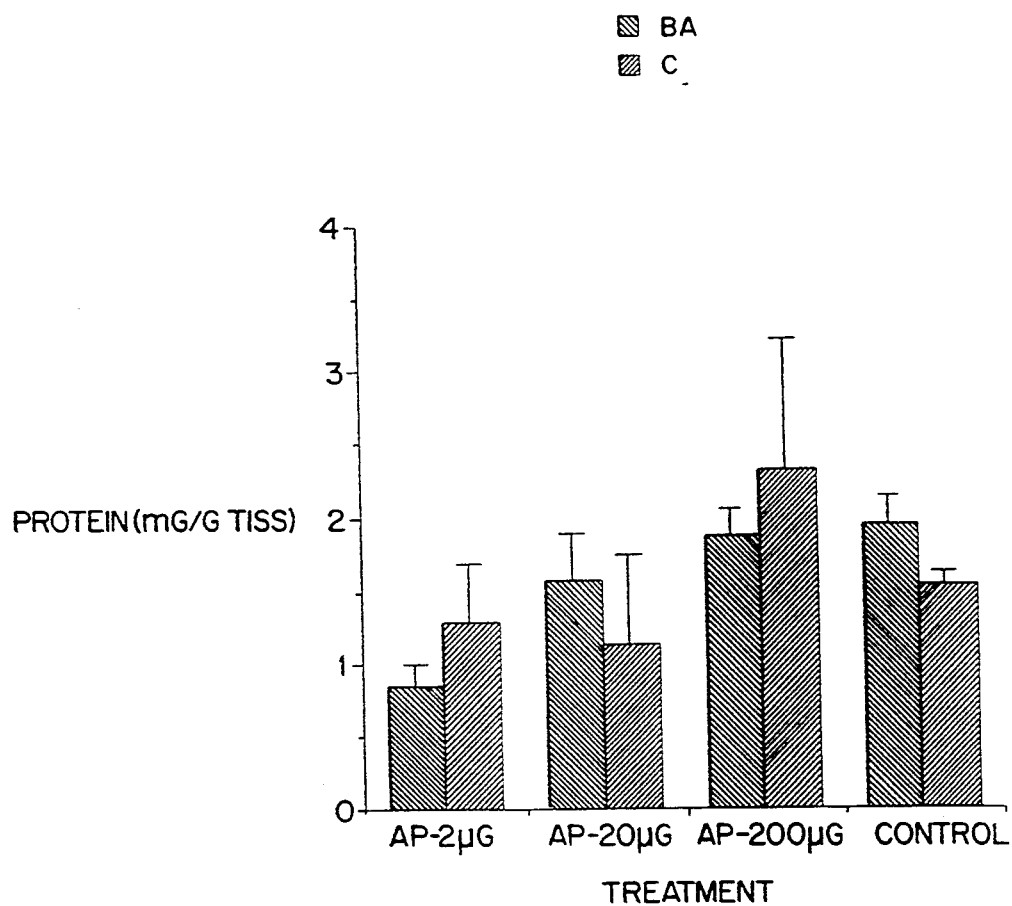
FIG. 2 is a graph showing the amount of protein in rabbit aortas after balloon angioplasty.

BA = Ballooned area of aorta
NBA = Non balloon area of aorta
Total = Total weight of aorta (BA+NBA) recovered from rabbits In FIG. 2

BA = Balloon angioplastic aortic area
C = Non ballooned aortic area
AP = Angiopeptin
N = 5

Figure 4:
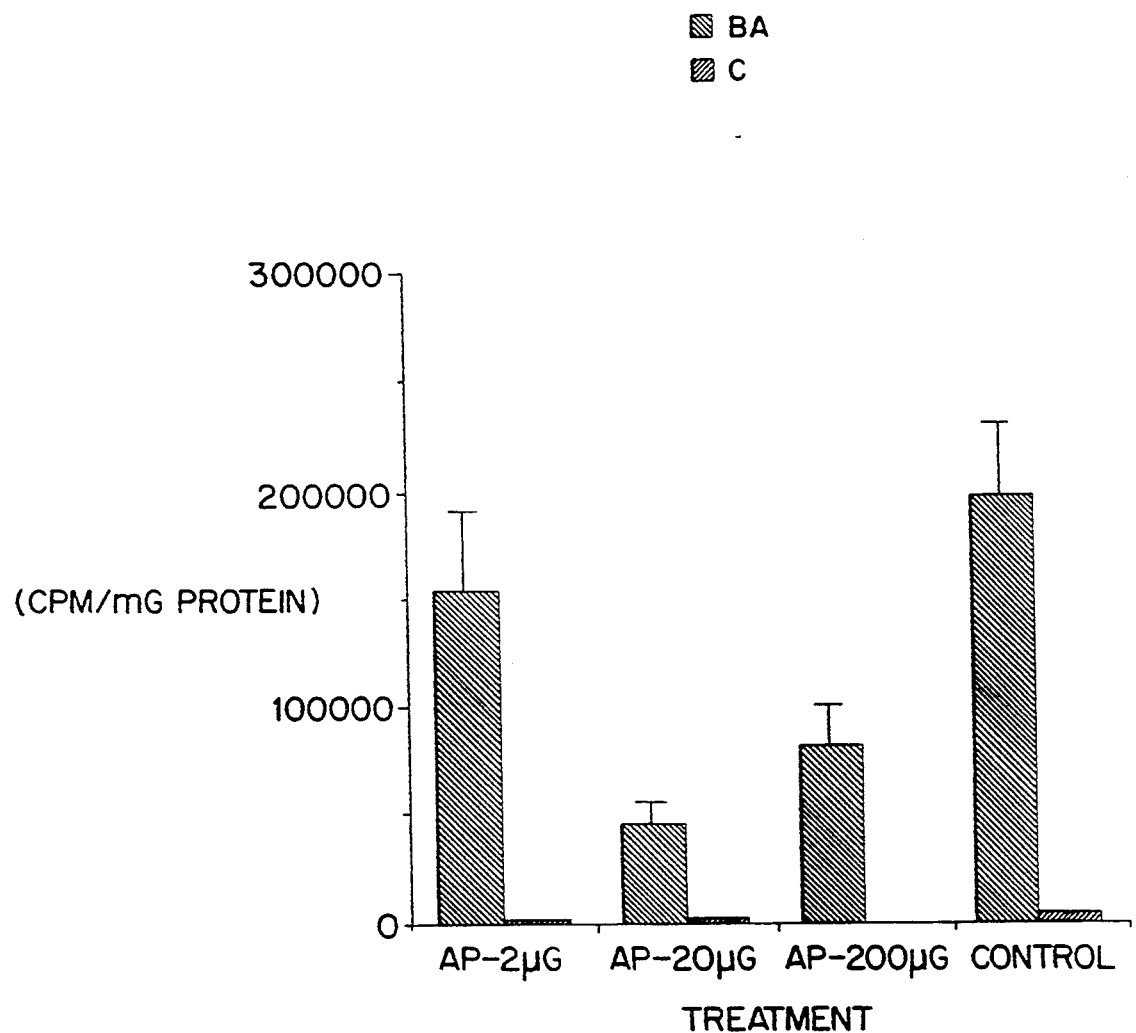
FIG. 4 is a graph showing 3-H Thymidine incorporation in rabbit aorta following balloon angioplasty.

In FIG. 4

BA = Ballooned aortic area
C = Non ballooned aortic area.

DESCRIPTION OF THE PREFERRED EMBODIMENTS

Structure

The compounds of the invention have the general formula recited in the Summary of the Invention, above. They are all octapeptide analogs of somatostatin which have D-Trp at position 4; and optional modifications at positions 3 ($A_4$), 6 ($A_5$), and 8 ($A_7$) D-beta-naphthylalanine at position 1; Tyr at position 3; and Val at position 6 are modifications which are particularly preferred.

The compounds can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic or carboxymethyl cellulose, and salts with inorganic acids, e.g., hydrochloric acid, sulfuric acid, or phosphoric acid.

Synthesis

The synthesis of one octapeptide follows. Other octapeptides suitable for use in the methods of the invention can be prepared by making appropriate modifications, within the ability of someone of ordinary skill in this field, of the following synthetic method.

EXAMPLE 1

D-Nal-Cys-Tyr-D-Trp-Lys-Val-Cys-Thr-$NH_2$
(Angiopeptin)

The first step in the preparation of

D-β-naphthylalanine-Cys-Tyr-D-Trp-Lys-Val-Cys-Thr-$NH_2$;

was the preparation of the intermediate tert-butyloxycarbonyl-D-β-naphthylalanine-S-methylbenzyl-Cys-Tyr-D-Trp-N-benzyloxycarbonyl-Lys-Val-S-methylbenzyl-Cys-O-benzyl-Thr-benzyhydrylaminic resin, as follows.

Benzhydrylamine-polystyrene resin (Vega Biochemicals, Inc.) in the chloride ion form was placed in the reaction vessel of a Beckman 990B peptide synthesizer programmed to perform the following reaction cycle: (a) methylene chloride; (b) 33% trifluoroacetic acid in methylene chloride (2 times for 1 and 25 min each); (c) methylene chloride; (d) ethanol; (e) methylene chloride; (f) 10% triethylamine in chloroform.

The neutralized resin was stirred with Boc-O-benzyl-threonine and diisopropylcarbodiimide (1.5 mmole each) in methylene chloride for 1 h and the resulting amino acid resin was then cycled through steps (a) to (b) in the above wash program. The following amino acids (1.5 mmole) were then coupled successively by the same procedure: Boc-S-methylbenzyl-Cys, Boc-Val, Boc-N-benzyloxycarbonyl-Lys, Boc-D-Trp, Boc-Tyr, Boc-S-methylbenzyl-Cys, Boc-D-β-naphthylalanine.

The resin was washed and dried and then mixed with anisole (4 ml) and anhydrous hydrogen fluoride (36 ml) at 0° C. and stirred for 45 min (one can also use thioanisole, trifluoroacetic acid, and trifluoromethane sulfonic acid at a ratio of 1:90:9, for 6 h). Excess hydrogen fluoride was evaporated rapidly under a stream of dry nitrogen and free peptide precipitated and washed with ether. The crude peptide was then dissolved in 800 ml of 90% acetic acid to which was added $I_2$ in methanol until a permanent brown color was present. The solution was then stirred for 1 h before removing the solvent in vacuo. The resulting oil was dissolved in a minimum volume to 50% acetic acid and eluted on a column (2.5 × 100 mm) of Sephadex G-25. Fractions containing a major component by uv absorption and thin layer chromatography were then pooled, evaporated to a small volume, and applied to a column (2.5 × 50 cm) of Whatman LRP-1 octadecylsilane (15-20 μM).

The column was eluted with a linear gradient of 10-50% acetonitrile in 0.1% trifluoroacetic acid in water. Fractions were examined by thin layer chromatography and HPLC and pooled to give maximum purity and, if desired, a different salt prepared, e.g., acetate or phosphate. Repeated lyophilization of the solution from water gave 170 mg of the product as a white, fluffy powder.

The product was found to be homogenous by HPLC and Tlc. Amino acid analysis of an acid hydrolysate confirmed the composition of the octapeptide.

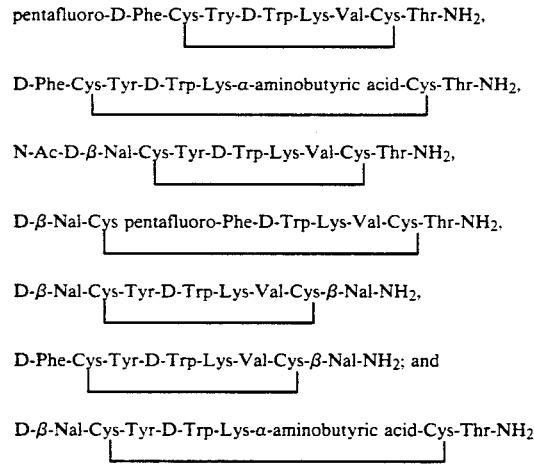

were made according to methods analogous to those described above.

EXAMPLE 2

Materials and Methods

Male Sprague-Dawley rats, weighing 250-350 mg, obtained from Charles River were kept under controlled lighting conditions and fed rat chow and water ad libitum. Under sodium pentobarbital anesthesia the intima of the right carotid artery was subjected to an air-drying injury described by Fishman et al, Lab Invest., 32, 339 (1975). The procedure causes intimal hyperplasia that largely consists of proliferating intimal smooth muscle cells. In this model approximately 4 cm of the vessel is isolated and drained of blood. Air (20 ml/min) is blown through a 30 gauge needle for 5 min whereafter blood flow is reestablished. The contralateral carotid artery was also exposed but not air-dried. The rats were sacrificed 15 days later.

The experiment consisted of a control group and ten treatment groups. The somatostatin analogs used were hepta- or octapeptides, namely BIM 23014 (Angiopeptin), BIM 23012, BIM 23027, BIM 23030 and BIM 23034. These compounds were all potent inhibitors of growth hormone release, see Table I (Heiman et al., Neuroendocrinology, 45, 429 (1987); Coy et al., In: Peptides. Escom, Leiden, pp. 462-463 (1988); and Tolis et al., Int. Congress Adv. in Growth Hormone and Growth Factor Research. Milan (1988) Abstract.) The peptides were administered at two different doses (20 μg/kg/day and 50 μg/kg/day s.c. in two divided doses). The animals were pretreated two days prior to the procedure and for a further five days following the endothelial injury. Two additional groups of animals were added in order to study whether Angiopeptin (20 μg/kg/day and 50 μg/kg/day) administered 30 min prior to the endothelial injury and for a further five days would protect against the myointimal proliferation.

The animals were sacrificed on day 15 following the injury by exsanguination. The vascular system was flushed with normal saline and perfusion-fixed at 80 mmHg with 10% formalin. The carotid arteries were subsequently fixed, embedded and sectioned for light microscopy and morphometric analysis. The maximal intimal/media ratio is the distance from the lumen to the internal elastic lamina and the distance from the internal elastic lamina to the external elastic lamina. The distances were determined in each vessel using a digitizing system attached to a light microscope. The determinations were performed on three different cross sections of the vessel and each section was measured three times. The mean was calculated for each vessel. Differences between the groups were evaluated using Student's unpaired t-test.

The results are shown in the following Table:

TABLE I

| Peptide | Amino Acid Sequence | Intimal/Media Ratio | |
|---|---|---|---|
| | | 20 μg/Kg | 50 μg/Kg |
| Vehicle | | 1.8 ± 0.4 (16) | |
| Angiopeptin | D-Nal—Cys—Tyr-D-Trp—Lys—Val—Cys—Thr—NH$_2$[a] | 1.7 ± 0.2#(7) | 1.1 ± 0.2* (6) |
| BIM 23034 | D-Phe—Cys—Tyr-D-Trp—Lys—Val—Cys—Nal—NH$_2$ | 1.9 ± 0.2 (3) | 1.2 ± 0.5* (6) |
| BIM 23030 | Mpa—Tyr-D-Trp—Lys—Val—Cys—Phe—NH$_2$ | 1.6 ± 0.2 (5) | 2.2 ± 0.5 (3) |
| BIM 23027 | D-Trp—Lys—Abu—Phe—Me—Ala—Tyr | 1.6 ± 0.2 (4) | 1.5 ± 0.2 (3) |
| BIM 23012 | D-Phe—Cys—Phe-D-Trp—Lys—Thr—Cys—Thr—NH$_2$[b] | 2.3 ± 0.4 (3) | 1.6 ± 0.4 (5) |

TABLE I-continued

| Peptide | Amino Acid Sequence | Intimal/Media Ratio 20 μg/Kg | 50 μg/Kg |
|---|---|---|---|
| Angiopeptin | (Pretreatment 30 min) | 1.6 ± 0.9 (7) | 1.0 ± 0.3 (6) |

The numbers in parenthesis indicate the number of rats in each group. The intimal/media ratio is the ratio of the distance from lumen to the internal elastic lamina to the distance from the internal to the external elastic lamina. The statistical significance of the difference of the means (±SE) of the ratios was analyzed with Students t-test. #P < 0.01 and *P < 0.05.
The rats were treated from two days prior to the endothelial injury and for five days postinjury.
The rank of potency of the peptides with respect to growth hormone suppression in vivo in rats compared to somatostatin 14 (=1) is Angiopeptin (5), BIM 23034 (2), BIM 23030 (0.5), BIM 23027 (100), and BIM 23012 (62).
$^a$D-Nal = 3-(2-Naphthyl)-D-Alanine;
$^b$Amide-Sandostatin instead of hydroxyl-Sandostatin.

Results

Angiopeptin and the closely related octapeptide BIM 23034 (Table I) inhibited significantly (P<0.01) myointimal proliferation of the carotid artery following endothelial injury by air drying. Both drugs were administered two days prior to the endothelial injury. Both the low (20 μg/kg/day) and high (50 μg/kg/day) doses of Angiopeptin and the higher dose (50 μg/kg/day) of BIM 23034 were effective. The other three somatostatin analogs, BIM 23012, BIM 23027 and BIM 23030 did not inhibit smooth muscle cell proliferation at the doses used. Angiopeptin 50 μg/kg/day administered prior to the arterial injury (30 min) and for a further five days significantly (p<0.01) inhibited myointimal proliferation.

Discussion

Inhibition of smooth muscle proliferation was observed 15 days after endothelial injury although subcutaneous administration of Angiopeptin and BIM 23034 was for only five days. This indicates that the signal for proliferation is an early event after endothelial injury. Thus Angiopeptin and BIM 23034 may interfere with the early effects of the different mitogens released at the time of vessel injury. The protective effect of Angiopeptin when administered as a short term pretreatment 30 min prior to the procedure also indicates an immediate antiproliferative effect.

A possible mechanism of action might be inhibition of growth hormone and thereby of insulin-like growth factor but binding to pituitary somatostatin receptors has been studied with Angiopeptin, BIM 23012 (Sandostatin) and BIM 23034 and the assays show a similar degree of binding for the three octapeptides (Coy et al, cited hereinabove). They are all potent inhibitors of growth hormone in vivo with BIM 23027 being the most potent. Since both Angiopeptin and BIM 23034 are less active in inhibition of release of growth hormone but are the ones active in inhibiting vascular smooth muscle proliferation, it is possible that the antiproliferative effect is unrelated to growth hormone secretion and indicates a direct effect of these two peptides on the vascular smooth muscle at the site of the injury.

It is possible that the endothelium may normally secrete an inhibitor of smooth muscle cell proliferation; in the absence of this putative endothelium autocrine inhibitor the smooth muscle cell may become highly responsive to chemotactic and mitogenic signals. This inhibitor and the two peptides described here may be related.

EXAMPLE 3

Effect of Angiopeptin on Myointimal Hyperplasia in Rabbits

Female and Male, white New Zealand rabbits (2.8-3.0 kg) were divided into two groups (A and B). Group A (vehicle control) received subcutaneous injections of physiological saline (0.2 ml) twice daily. Group B received subcutaneous injections (0.2 ml, twice daily) of Angiopeptin (20 μg/kg twice daily) dissolved in physiological saline. The animals were treated the day before angioplasty, and until sacrifice about 3 weeks later. The angioplasty was done under general anesthesia with Ketamine and Xylazine. Each animal's left iliac artery and aorta were denuded with an angioplasty catheter (Fogarty). The angioplasty catheter was inserted into the left femoral artery and passed through the vessel to the thoracic aorta. The catheter was then reciprocated three times. The animals were all sacrificed from days 22-24 after angioplasty. The aorta and iliac arteries were fixed in situ via perfusion with formaldehyde under constant perfusion pressure.

Intimal hyperplasia was determined on elastin-stained (Van Giesen) horizontally-cut sections. The sections were obtained from (i) the aorta at the level of the renal artery, (ii) the common iliac artery at the level of bifurcation, and (iii) the external iliac artery just above the inguinal ligament. The area of intimal hyperplasia and total vessel area were determined by morphometry. The percentage of intimal hyperplasia was expressed as follows:

$$\% \text{ intimal hyperplasia} = \frac{\text{area of intimal hyperplasia}}{\text{total vessel area}} \times 100$$

Single determinations were made on three segments of each aorta and the two iliac arteries of each animal. The percentage of intimal hyperplasia was determined as the mean of the two closest measurements of each vessel.

In the control group, the myointimal hyperplasia was greatest in the external iliac artery, where the percentage of intimal hyperplasia was 34.7%±11.5% (female rabbits) and 30. 0%±6.3% (male rabbits). The percentage of intimal hyperplasia appeared to decrease with increasing vessel size, as the common iliac artery and the aorta showed percentages of intimal hyperplasia of 23.7%±4.9 and 18.8%±2.9%, respectively (female rabbits) and 23.0%±5.8% and 22.0±6.5%, respectively (male rabbits). The percentage of inhibition of myointimal hyperplasia by Angiopeptin (20 μg/kg/d) was significant and similar for all three vessel segments, about 41%, 33% and 43% for the external iliac artery, common iliac artery, and aorta, respectively in female rabbits and 20%, 39% and 32%, respectively, in male rabbits. The results are shown in the following Tables.

TABLE II

EFFECT ON INTIMAL HYPERPLASIA IN THE
EXTERNAL ILIAC ARTERY OF FEMALE RABBITS

| Samples | Control | Angiopeptin |
|---|---|---|
|  | (% Intimal hyperplasia) | |
| 1 | 26.9 | 26.4 |
| 2 | 57.5 | 15.2 |
| 3 | 28.6 | 21.3 |
| 4 | 33.2 | 33.6 |
| 5 | 33.6 | 24.1 |
| 6 | 26.1 | 20.6 |
| 7 | — | 6.6 |
| 8 | — | 17.8 |
| Mean | 34.7 | 20.7 |
| SD | 11.5 | 8.0 |
| t-statistic |  | 2.679 |
| Degrees of Freedom |  | 12 |
| Significance |  | 0.020 |

TABLE III

Effect on Intimal Hyperplasia in the
Common Iliac Artery of Female Rabbits

| Samples | Control | Angiopeptin |
|---|---|---|
|  | (% Intimal hyperplasia) | |
| 1 | 26.0 | 9.3 |
| 2 | 30.6 | 9.5 |
| 3 | 19.2 | 19.7 |
| 4 | 18.8 | 20.5 |
| 5 | 27.1 | 15.3 |
| 6 | 20.4 | 16.6 |
| 7 | — | 7.7 |
| 8 | — | 6.5 |
| Mean | 23.7 | 13.1 |
| SD | 4.9 | 5.6 |
| t-statistic |  | 3.706 |
| Degrees of Freedom |  | 12 |
| Significance |  | 0.003 |

TABLE IV

Effect on Intimal Hyperplasia in the
Aorta of Female Rabbits

| Samples | Control | Angiopeptin |
|---|---|---|
|  | (% Intimal hyperplasia) | |
| 1 | 19.0 | 13.0 |
| 2 | 20.9 | 10.7 |
| 3 | 14.1 | 12.8 |
| 4 | 22.4 | 19.5 |
| 5 | 17.6 | 6.4 |
| 6 | 18.4 | — |
| Mean | 18.8 | 12.5 |
| SD | 2.9 | 4.7 |
| t-statistic |  | 2.726 |
| Degrees of Freedom |  | 9 |
| Significance |  | 0.023 |

TABLE V

Effect on Intimal Hyperplasia in the
External Iliac Artery of Male Rabbits

| Samples | Control | Angiopeptin |
|---|---|---|
|  | (% Intimal hyperplasia) | |
| 1 | 30.3 | 30.5 |
| 2 | 24.5 | 19.2 |
| 3 | 33.7 | 25.7 |
| 4 | 25.4 | 26.5 |
| 5 | 42.2 | 22.3 |
| 6 | 27.2 | 37.9 |
| 7 | 26.5 | 22.2 |
| Mean | 30.0 | 24.4 |
| SD | 6.3 | 4.0 |
| t-statistic |  | 1.860 |
| Degree of Freedom |  | 11 |

TABLE V-continued

Effect on Intimal Hyperplasia in the
External Iliac Artery of Male Rabbits

| Samples | Control | Angiopeptin |
|---|---|---|
|  | (% Intimal hyperplasia) | |
| Significance |  | 0.090 |

TABLE VI

Effect on Intimal Hyperplasia in
Common Iliac Artery of Male Rabbits

| Samples | Control | Angiopeptin |
|---|---|---|
|  | (% Intimal hyperplasia) | |
| 1 | 27.6 | 14.9 |
| 2 | 24.0 | 16.0 |
| 3 | 24.1 | 6.4 |
| 4 | 17.6 | 17.4 |
| 5 | 30.4 | 13.9 |
| 6 | 23.9 | 15.8 |
| 7 | 13.2 | 14.0 |
| Mean | 23.0 | 14.1 |
| SD | 5.8 | 3.6 |
| t-statistic |  | 3.439 |
| Degrees of Freedom |  | 12 |
| Significance |  | 0.005 |

TABLE VII

Effect on Intimal Hyperplasia in the
Aorta of Male Rabbits

| Samples | Control | Angiopeptin |
|---|---|---|
|  | (% Intimal hyperplasia) | |
| 1 | 27.5 | 15.9 |
| 2 | 13.7 | 17.0 |
| 3 | 17.9 | 12.4 |
| 4 | 29.3 | 13.3 |
| 5 | 21.3 | 13.8 |
| 6 | 4.6 | 15.7 |
| 7 | — | 15.7 |
| Mean | 22.0 | 14.8 |
| SD | 6.5 | 1.7 |
| t-statistic |  | 2.810 |
| Degrees of Freedom |  | 10 |
| Significance |  | 0.018 |

EXAMPLE 4

Angiopeptin was administered s.c. twice a day 50 µg/kg/day to male Sprague-Dawley (Charles River) rats, 250–350 g each. After two days of pre-treatment, a lesion was made on the third day after the morning dose by air-drying the right carotid artery while the rats were under anesthesia (Ketamine-Innovar, i.m.). Treatment was continued on day: 4, 5, 6, and 7. The rats were sacrificed on day 14 following the injury. After in-situ fixation at constant pressure, with 10% formalin, the tissues were prepared to form morphometrics.

Hyperplasia was measured as the ratio of width of intimal and medial layers. For each rat, 3 different histological sections were measured and the morphometrics was done 3 times on each section. The results are shown in the following Table.

TABLE VIII

| No-Treatment | Treatment 50 µg |
|---|---|
| 1.51 + 0.07 | 0.46 + 0.08 |
| 1.22 + 0.08 | 0.28 + 0.03 |
| 1.28 + 0.05 | 0.52 + 0.05 |
| 1.96 + 0.2 | 0.69 + 0.02 |
| 1.77 + 0.14 | |

Statistics: Student's t-test was performed to assess the significance of the data.

TABLE VIII-continued

| File name | No-treatment | Treatment 50 μg |
|---|---|---|
| N | 5 | 4 |
| Minimum | 1.22 | 0.28 |
| Mean | 1.54 | 0.48 |
| Maximum | 1.96 | 0.69 |
| Sum | 7.74 | 1.95 |
| Std Dev | 0.31 | 0.16 |
| Std Error | 0.14 | 8.45–02 |
| 95% C.L. | 0.39 | 0.26 |

| No-treatment vs. | Treatment | Pooled Variance 6.93–02 |
|---|---|---|
| t(95%) | 2.36 | 7 d.f. |
| t(99%) | 3.49 | |
| t(cal) | 6.00 | Significant at $p < 0.01$ |

EXAMPLE 5

In order to obtain a primate coronary angioplasty model which would be suited for evaluation of Angiopeptin, a feasibility study was performed on primates which were made available from the colony at Bowman-Gray Medical School, Winston-Salem, North Carolina. These animals were culled from the colony due to failure of the primates to satisfactorily elevate blood lipids when administered a high cholesterol diet. Young male cynomologous macaques weighing approximately 3.5 kg were used after an equilibration period of more than a week in a primate facility.

The animals were sedated with Ketamine and maintained with 1% halothane in oxygen. The aorta and femoral arteries were injured by a balloon catheter (USCI, Band). After five weeks the primates were anesthetized and sacrificed. The aorta and femoral arteries were removed and fixed in formaldehyde for morphometric analysis.

To avoid the stress of twice daily injections, Angiopeptin was administered i.m. to a male cynomologous macaque in a slow release system two days prior to the procedure and again at the time of the ballooning. Each injection had a calculated daily release of 25 μg/kg, which is a total of 50 μg/kg/day (IPSEN International, Paris).

The maximal intimal/media ratio (distance from lumen to internal elastic lamina/distance from internal elastic lamina to external elastic lamina) was determined in each vessel using a digitizing system attached to a light microscope. The determinations were done on three different cross sections of the vessel and each section was measured three times and each three measurements were averaged.

This size of primate was found to be too small for reproducible access to the coronaries. It is recommended that larger macaques of at least 7.5 kg be used. Attempts to use low dose heparin lead to carotid thrombosis and stroke following carotid artery angioplasty. The use of heparin is recommended and carotid artery angioplasty should be avoided due to the risk of complications requiring premature euthanasia of the animals.

Of two primates which survived ballooning of the peripheral vessels, one had been treated with Angiopeptin and the other was untreated.

The Angiopeptin treated primate exhibited nearly complete inhibition of smooth muscle cell proliferation in the aorta and both left and right femoral arteries compared to the control animal.

EXAMPLE 6

New Zealand White Rabbits were anesthetised with Rompun (Xylazine) and Ketalar (Ketamine) and a cannula (3F Fogarty) was inserted from the femoral artery. The balloon was inflated at a constant pressure and the aorta was de-endothelialised by angioplasty. The process was repeated three times and the wound site was closed. The animals were sacrificed 72 hours after balloon angioplasty and after removing the adventitia the aorta was cut into fine rings. These rings were incubated in the presence of 3-H thymidine and the radioactivity was determined after processing the tissue. Simultaneous measurements of DNA and protein contents were also made in these tissues.

Eight injections of Angiopeptin were made: on the morning and evening of the day prior to ballooning; two on the day of the procedure; and two on each of the following two days. The total daily dose was 2, 20, or 200 μg/Kg body weight.

Three doses of angiopeptin (2 μg, 20 μg and 200 μg/kg body wt.) were tested to exhibit the inhibitory effects of drug on the myointimal cell proliferation in the aortas of rabbits following balloon angioplasty.

Figure 1:
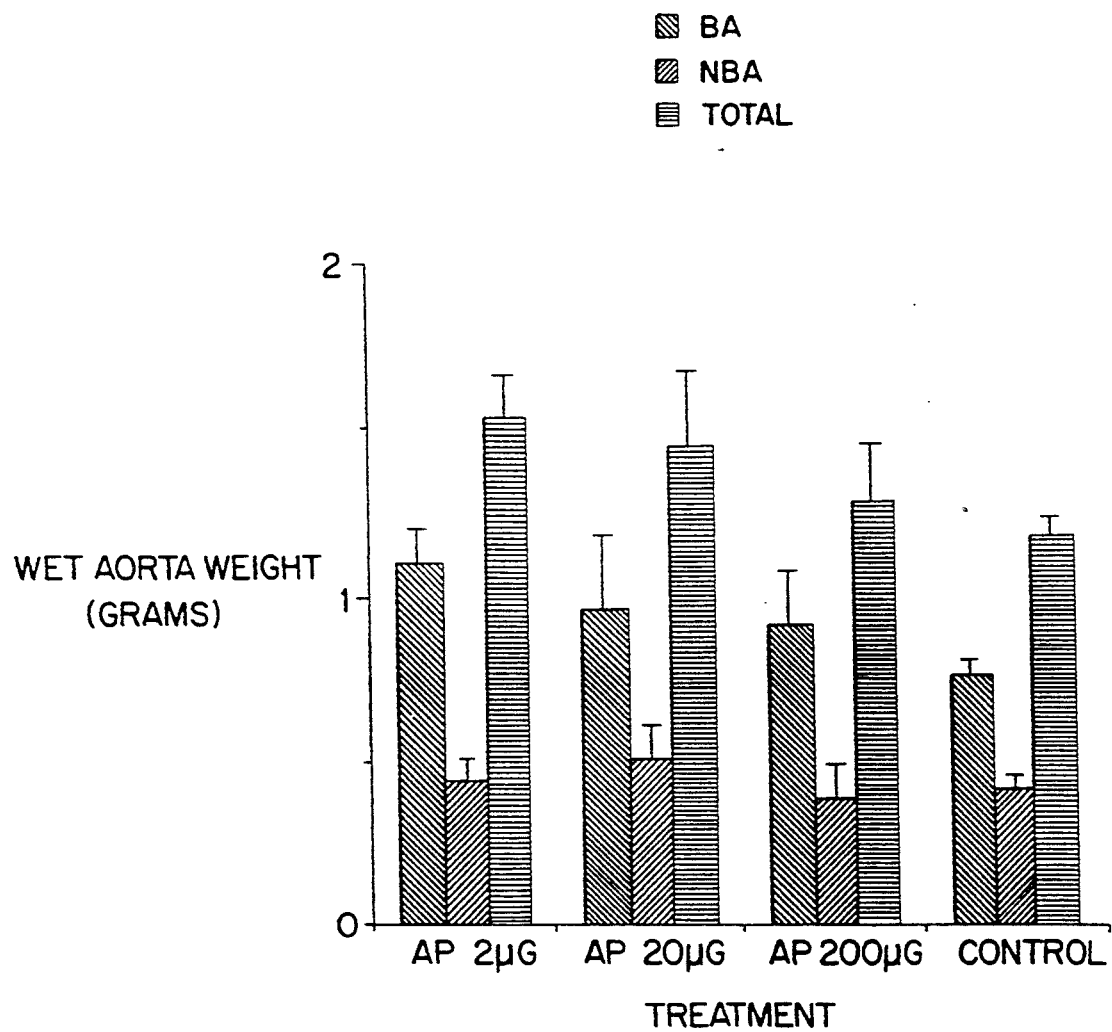
FIG. 1 is a graph showing the net weight of rabbit aortas following balloon angioplasty.
Figure 3:
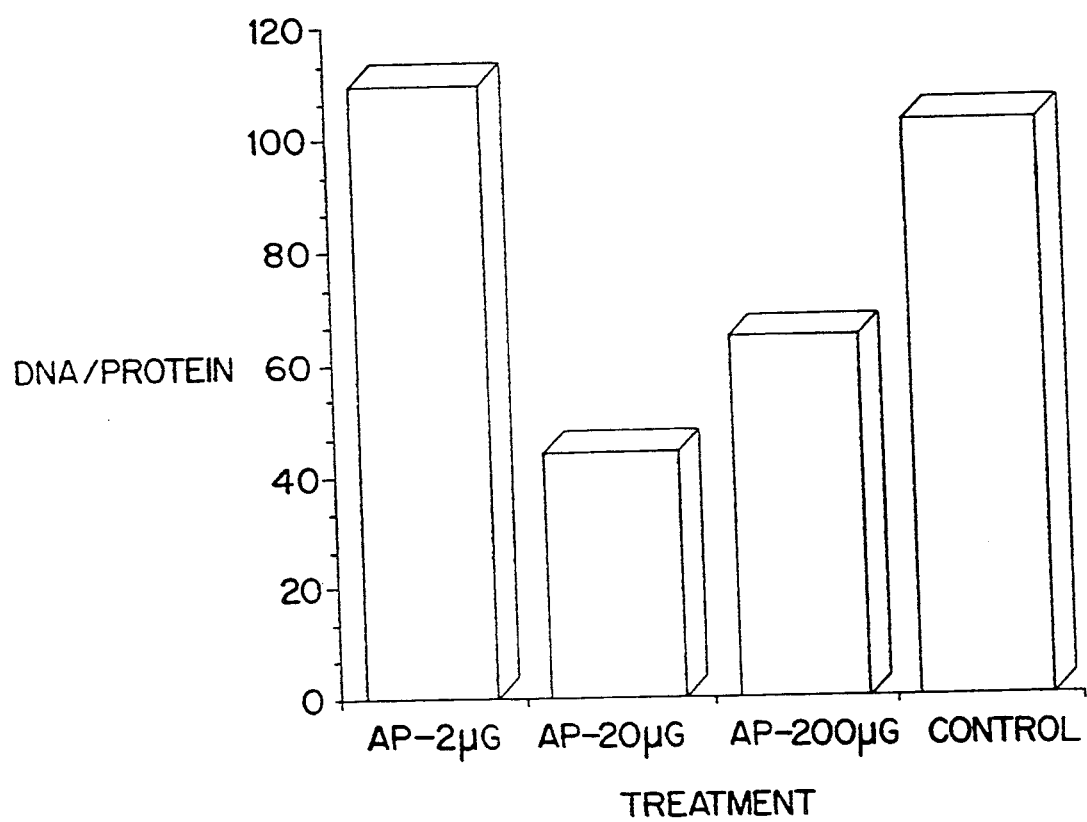
FIG. 3 is a graph showing the DNA/Protein ratio in rabbit aortas after balloon angioplasty.

1. Wet Weight: In general this drug does not seem to influence the wet weight of aortas. There were no differences in the wet weight of non-ballooned areas. However, the ballooned areas of the aorta had marginally higher wet weights which could be due to variation in the hydration of the tissues. The results are shown in FIG. 1.
2. Levels of Proteins: At lower doses (2 μg) angiopeptin lowered the total protein content of the injured aortas following balloon angioplasty. Higher doses of angiopeptin did not affect the levels of total proteins as no significant differences were seen in the control and treated aortas. The results are shown in FIG. 2.
3. DNA/Protein Ratio: Angiopeptin 20 μg/kg body weight significantly lowered the DNA/Protein ratio, indicating thereby its inhibitory effect of the myointimal proliferation of rabbit aortas. Higher doses (200 μg/kg body wt.) also reflected the inhibitory influence of this drug. The results are shown in FIG. 3.
4. Thymidine (3-H) Incorporation: The rates of cell proliferation (myointimal proliferation) were monitored by incorporation of 3-H TdR in the rabbit aortas after balloon angioplasty and it was observed that angiopeptin significantly inhibited the rates of cell proliferation. A dose of 20 μg/kg body wt. was found to significantly lower the rates of cell proliferation after balloon angioplasty. Higher doses, i.e., 200 μg/kg still inhibited the myointimal proliferation, however, the degree of inhibition was less than that 20 μg dose. The results are shown in FIG. 4.

EXAMPLE 7

Effect of Angiopeptin on the Proliferation of Smooth Muscle Pig Left Coronary Artery Explants.

METHODS

Domestic pig hearts were obtained from a slaughter house immediately after the animals were sacrificed. The hearts were harvested and placed in ice-cold Kreb's Ringer buffer and transported to the laboratory. The left coronary artery (LAD) was dissected in aseptic conditions and divided into pieces of 5 mm. The segments were denuded from the endothelium by gently introducing a metallic rod in the lumen. The tissues were placed in sterile multiwell culture dishes in 1 ml of culture media (DMEM with antibiotics) and without fetal calf serum. $H^3$-thymidine (2.5 uCi/ml) and increasing concentrations of angiopeptin (10-1000 ng/ml) were added to the medium. Segments which were incubated with 3 different concentrations of forskolin were used as a positive control in each experiment. The incubation period was 24 hr at 37° C. and 5% $CO_2$. The tissues were washed with phosphate saline buffer and placed in a solution of cold thymidine for one hour and then frozen in liquid nitrogen, ground and lysed with a hypotonic solution. The lysed tissues were further incubated with proteinase K overnight at 50° C. The radioactivity, content of protein and DNA were measured.

RESULTS:

| CPM | Protein | CPM/mg | Angiopeptin |
|---|---|---|---|
| 35113.84 | 3.6 mg | 9.753.8 | 10 ng/ml |
| 46392.32 | 3.4 | 13.644.8 | 10 |
| 27312.80 | 3.7 | 7.381.8 | 10 |
| 55980.00 | 4.0 | 13.995.0 | 10 |
| 26279.81 | 3.6 | 7.299.7 | 20 |
| 39027.27 | 4.1 | 9.518.8 | 20 |
| 39706.01 | 4.7 | 8.448.1 | 20 |
| 21562.08 | 4.2 | 5.133.8 | 20 |
| 18942.16 | 3.9 | 4.857.0 | 50 |
| 24269.18 | 3.9 | 6.222.9 | 50 |
| 40768.09 | 3.6 | 11.324.4 | 50 |
| 18983.78 | 3.2 | 5.932.4 | 50 |
| 20794.85 | 3.9 | 5.332.01 | 100 |
| 32402.31 | 5.0 | 6.480.5 | 100 |
| 22033.48 | 3.7 | 5.955.0 | 100 |
| 26227.64 | 4.1 | 6.397.0 | 100 |
| 18325.51 | 2.8 | 6.544.8 | 1000 g/ml |
| 27260.98 | 4.6 | 5.926.3 | 1000 |
| 30226.99 | 4.6 | 6.571.1 | 1000 |
| 32344.58 | 4.6 | 7.031.4 | 1000 |

SUMMARY:

| DOSE (ng/ml) | RESPONSE (cpm/mg) |
|---|---|
| 10 | 11.119.9 ± 1593.2 |
| 20 | 7.600.1 ± 938.7 |
| 50 | 7.084.2 ± 1443.6 |
| 100 | 6.041.1 ± 263.0 |
| 1000 | 6.518.4 ± 226.8 |

What is claimed is:

1. A method for inhibiting blood vessel blockage in a mammal, which comprises: administering to a mammal an effective blood vessel blockage inhibiting amount of an octapeptide having the formula

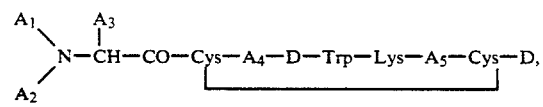

L—A$_7$—Z wherein each $A_1$ and $A_2$, independently, in H, $C_{1-12}$ alkyl, $C_{7-10}$ phenylalkyl, $R_1CO$ wherein $R_1$ is $C_{1-20}$ alkenyl, $C_{3-20}$ alkenyl, $C_{3-20}$ alkinyl, phenyl, naphthyl, or $C_{7-100}$ phenylalkyl, or $R_2OCO$ wherein $R_2$ is $C_{1-10}$ alkyl or $C_{7-20}$ phenylalkyl, provided that when one of $A_1$ or $A_2$ is $R_1CO$ or $R_2OCO$, the other must be H; $A_3$ is $CH_2A_6$ wherein $A_6$ is pentafluorophenyl, naphthyl, pyridyl, or phenyl); $A_4$ is o-, m- or, p-substituted X-Phe wherein X is a halogen, H, $NH_2$, $NO_2$, OH, or $C_{1-13}$ alkyl, pentafluoro-Phe, $\beta$-Nal or Tyr; $A_5$ is Thr, Ser, Phe, Val, $\alpha$-aminobutyric acid, or Ile; $A_7$ is Thr, Trp, or $\beta$-Nal and can be either the D- or L-isomer; and Z is $NH_2$ or OH; or a pharmaceutically acceptable salt thereof.

2. The method of claim 1, wherein said octapeptide is administered shortly before, during or within six months after angioplasty.

3. The method of claim 2, wherein said octapeptide is administered for at least 24 hours prior to angioplasty.

4. The method of claim 1, wherein in the administered octapeptide Z is $NH_2$ and

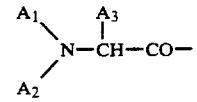

is D-$\beta$-napthylalanine.

5. The method of claim 1, wherein the octapeptide is administered subcutaneously.

6. The method of claim 1, wherein the octapeptide is administered in a dosage of 1-100 μg/kg/day.

7. A method for inhibiting blood vessel blockage in a mammal after angioplasty, an arterial by-pass operation or an allograft transplant operation, which comprises: administering to a patient by injecting 1-100 μg/kg/day of an octapeptide of the formula

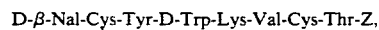

D-$\beta$-Nal-Cys-Tyr-D-Trp-Lys-Val-Cys-Thr-Z, wherein Z is $NH_2$ or OH, or a pharmaceutically acceptable salt thereof, for at least 24 hours prior to angioplasty, an arterial by-pass operation or an allograft transplant operation.

8. The method of claim 7, wherein administration of continued after angioplasty.

9. The method of claim 8, wherein said octapeptide is administered subcutaneously.

10. A method for inhibiting blood vessel damage in a mammal which comprises administering to a mammal an effective blood vessel blockage inhibiting amount of an octapeptide having the formula

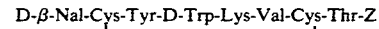

D-$\beta$-Nal-Cys-Tyr-D-Trp-Lys-Val-Cys-Thr-Z wherein Z is $NH_2$ or OH;
or a pharmaceutically acceptable salt thereof.

11. The method of claim 10, wherein said octapeptide is administered shortly before, during or within said months after angioplasty.

12. The method of claim 10, wherein said octapeptide is administered subcutaneously.

13. The method of claim 10, wherein said octapeptide is administered in a dosage of 1-100 μg/kg/day.

14. The method of claim 1, wherein said ocatapeptide is

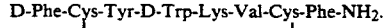

D-Phe-Cys-Tyr-D-Trp-Lys-Val-Cys-Phe-$NH_2$.

15. The method of claim 1, wherein said octapeptide is

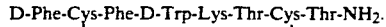

D-Phe-Cys-Phe-D-Trp-Lys-Thr-Cys-Thr-$NH_2$.

* * * * *